US00PP22157P2

(12) United States Plant Patent
Elliot

(10) Patent No.: US PP22,157 P2
(45) Date of Patent: Sep. 20, 2011

(54) ***CUPHEA* PLANT NAMED 'MAGENTA BORDER'**

(50) Latin Name: *Cuphea hyssopifolia*
Varietal Denomination: Magenta Border

(75) Inventor: Rodger Elliot, Cranbourne (AU)

(73) Assignee: Outback Plants Pty. Ltd., Cranbourne, Victoria (AU)

( * ) Notice: Subject to any disclaimer, the term of this patent is extended or adjusted under 35 U.S.C. 154(b) by 0 days.

(21) Appl. No.: 12/799,849

(22) Filed: May 4, 2010

(51) Int. Cl.
*A01H 5/00* (2006.01)

(52) U.S. Cl. ..... Plt./420

(58) Field of Classification Search ..... Plt./420
See application file for complete search history.

*Primary Examiner* — June Hwu
(74) *Attorney, Agent, or Firm* — C. A. Whealy

(57) ABSTRACT

A new and distinct cultivar of *Cuphea* plant named 'Magenta Border', characterized by its compact and mounding growth habit; freely branching habit; freely flowering habit; relatively large red purple-colored flowers; and good garden performance.

2 Drawing Sheets

Botanical designation: *Cuphea hyssopifolia.*
Cultivar denomination: 'MAGENTA BORDER'.

BACKGROUND OF THE INVENTION

The present invention relates to a new and distinct cultivar of *Cuphea* plant, botanically known as *Cuphea hyssopifolia* and hereinafter referred to by the name 'Magenta Border'.

The new *Cuphea* plant is a product of a planned breeding program conducted by the Inventor in Cranbourne, Victoria, Australia. The objective of the breeding program is to create new compact *Cuphea* plants with numerous attractive flowers and good garden performance.

The new *Cuphea* plant originated from an open-pollination during the spring of 2004 in Cranbourne, Victoria, Australia of an unnamed seedling selection of *Cuphea hyssopifolia,* not patented, as the female, or seed, parent with an unknown selection of *Cuphea hyssopifolia* as the male, or pollen, parent. The new *Cuphea* plant was discovered and selected by the Inventor as a single flowering plant within the progeny of the stated open-pollination in a controlled greenhouse environment in Cranbourne, Victoria, Australia during the spring of 2005.

Asexual reproduction of the new *Cuphea* plant by cuttings in a controlled greenhouse environment in Cranbourne, Victoria, Australia since the spring of 2005, has shown that the unique features of this new *Cuphea* plant are stable and reproduced true to type in successive generations.

SUMMARY OF THE INVENTION

Plants of the new *Cuphea* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Magenta Border'. These characteristics in combination distinguish 'Magenta Border' as a new and distinct cultivar of *Cuphea* plant:

1. Compact and mounding growth habit.
2. Freely branching habit.
3. Freely flowering habit.

4. Relatively large red purple-colored flowers.
5. Good garden performance.

Plants of the new *Cuphea* can be compared to plants of the female parent selection. Plants of the new *Cuphea* differ from plants of the female parent selection in the following characteristics:

1. Plants of the new *Cuphea* are more mounding than and not as upright as plants of the female parent selection.
2. Plants of the new *Cuphea* are shorter than plants of the female parent selection.
3. Plants of the new *Cuphea* have darker red purple-colored flowers than plants of the female parent selection.

Plants of the new *Cuphea* can also be compared to plants of the *Cuphea hyssopifolia* 'Southern Border', disclosed in a U.S. Plant Patent application filed concurrently. In side-by-side comparisons conducted in Cranbourne, Victoria, Australia, plants of the new *Cuphea* differed from plants of 'Southern Border' in the following characteristics:

1. Plants of the new *Cuphea* were more compact than plants of 'Southern Border'.
2. Plants of the new *Cuphea* were slower growing than plants of 'Southern Border'.
3. Plants of the new *Cuphea* and 'Southern Border' differed in flower color as plants of 'Southern Border' had purple-colored flowers.

BRIEF DESCRIPTION OF THE PHOTOGRAPHS

The accompanying colored photographs illustrate the overall appearance of the new *Cuphea* plant showing the colors as true as it is reasonably possible to obtain in colored reproductions of this type. Colors in the photographs may differ slightly from the color values cited in the detailed botanical description which accurately describe the colors of the new *Cuphea* plant.

The photograph on the first sheet comprises a top perspective view of a typical flowering plant of 'Magenta Border' grown in a container.

The photograph on the second sheet is a close-up view of typical flowers of 'Magenta Border'.

DETAILED BOTANICAL DESCRIPTION

The aforementioned photographs and following observations, measurements and values describe plants grown during the summer and autumn in 15-cm containers in a polyethylene-covered greenhouse in Cranbourne, Victoria, Australia and under cultural conditions which approximate commercial *Cuphea* plant production. During the production of the plants, day temperatures ranged from 12° C. to 40° C., night temperatures ranged from 6° C. to 28° C. and light levels ranged from 1,000 to 9,000 foot-candles. Rooted young plants were pinched one time and were four months old when the photographs and description were taken. In the following description, color references are made to The Royal Horticultural Society Colour Chart, 1995 Edition, except where general terms of ordinary dictionary significance are used.

Botanical classification: *Cuphea hyssopifolia* 'Magenta Border'.

Parentage:

*Female, or seed, parent.*—Unnamed seedling selection of *Cuphea hyssopifolia,* not patented.

*Male, or pollen, parent.*—Unknown selection of *Cuphea hyssopifolia,* not patented.

Propagation:

*Type.*—By cuttings.

*Time to initiate roots, summer.*—About 12 to 20 days at 22° C. to 30° C.

*Time to initiate roots, winter.*—About 18 to 30 days at 10° C. to 15° C.

*Time to produce a rooted young plant, summer.*—About 20 to 30 days at 16° C. to 39° C.

*Time to produce a rooted young plant, winter.*—About 25 to 45 days at 10° C. to 15° C.

*Root description.*—Fine, fibrous; white in color.

*Rooting habit.*—Freely branching; dense.

Plant description:

*Plant and growth habit.*—Herbaceous annual; compact and mounding growth habit; freely branching habit; moderately vigorous growth habit.

*Plant height.*—About 10 cm to 15 cm.

*Plant diameter.*—About 15 cm to 20 cm.

Lateral branch description:

*Length.*—About 3 cm to 10 cm.

*Diameter.*—About 2 mm.

*Internode length.*—About 0.2 cm to 5.5 cm.

*Aspect.*—About 60° to 90° from vertical.

*Texture.*—Sparsely pubescent.

*Color, young stems.*—Close to 174A.

*Color, developed stems.*—Close to 138A.

Foliage description:

*Arrangement.*—Opposite, occasionally alternate; simple.

*Length.*—About 0.8 cm to 2.6 cm.

*Width.*—About 3 mm to 7 mm.

*Shape.*—Oblong to narrowly elliptic.

*Apex.*—Bluntly acute.

*Base.*—Blunt.

*Margin.*—Entire; slightly recurved.

*Texture, upper and lower surfaces.*—Smooth, glabrous.

*Venation pattern.*—Pinnate.

*Color.*—Developing leaves, upper and lower surfaces: Close to 144A to 144B. Fully developed leaves, upper surface: Close to 147A; towards the margins, close to 59A; venation, close to 138B. Fully developed leaves, lower surface: Close to 146B; venation, close to 138B.

*Petiole length.*—About 1 mm.

*Petiole diameter.*—About 1 mm.

*Petiole texture, upper surface.*—Pubescent.

*Petiole texture, lower surface.*—Smooth, glabrous.

*Petiole color, upper and lower surfaces.*—Close to 138B.

Flower description:

*Flower arrangement and habit.*—Single tubular flowers with flaring petals; flowers arising from leaf axils; freely flowering habit with about four to eight flowers and flower buds per lateral stem; flowers face upright to outwardly.

*Fragrance.*—None detected.

*Natural flowering season.*—Plants flower continuously from the spring through the fall in Victoria, Australia; plants begin flowering about six to nine weeks after planting.

*Flower longevity.*—Individual flowers last about six to ten days on the plant; flowers not persistent.

*Flower diameter.*—About 9 mm to 11 mm.

*Flower length.*—About 8 mm to 10 mm.

*Flower bud.*—Shape: Cylindrical. Length: About 4 mm to 5 mm. Diameter: About 1 mm to 2 mm. Color: Close to 145A; towards the apex, close to 145D.

*Petals.*—Arrangement: Six petals arranged in a single whorl. Length: About 4 mm to 5 mm. Width: About 2 mm to 4 mm. Shape: Broadly elliptic. Apex: Rounded with blunt point. Base: Broadly tapering. Margin: Entire. Texture, upper and lower surfaces: Smooth, glabrous; crinkled. Color: When opening and fully opened, upper surface: Close to 71A; with development, color becoming closer to 72A. When opening and fully opened, lower surface: Close to 71A; with development, color becoming closer to 72B. Flower tube: Close to 155D. Flower throat: Close to 154D.

*Sepals.*—Arrangement: Six sepals fused in a single whorl; calyx, narrowly campanulate. Length: About 1 mm. Width: About 1 mm. Shape: Triangular. Apex: Shortly pointed. Base: Obtuse. Margin: Entire. Texture, upper and lower surfaces: Smooth, glabrous. Color, upper and lower surfaces: Close to 145A; towards the apex, close to 184B.

*Peduncles.*—Length: About 4 mm. Diameter: About 0.5 mm. Angle: About 60° from stem axis. Strength: Fairly weak. Texture: Smooth, glabrous. Color: Close to 191A; towards the apex, close to 186A.

*Reproductive organs.*—Stamens: Quantity per flower: About eleven. Pollen amount: Scarce. Pollen color: Close to 4D. Pistils: Quantity: One per flower. Pistil length: About 7 mm. Style length: About 6 mm. Style color: Close to 155D. Stigma color: Close to 155C. Ovary color: Close to 155A to 155D.

*Seeds.*—Quantity: Numerous seeds are produced.

Garden performance: Plants of the new *Cuphea* have been observed to have good garden performance and tolerate wind, rain and to tolerate temperatures ranging from −1° C. to 45° C.

Pathogen/pest resistance: Plants of the new *Cuphea* have not been observed to be resistant to pathogens and pests common to *Cuphea* plants.

It is claimed:

1. A new and distinct *Cuphea* plant named 'Magenta Border' as illustrated and described.

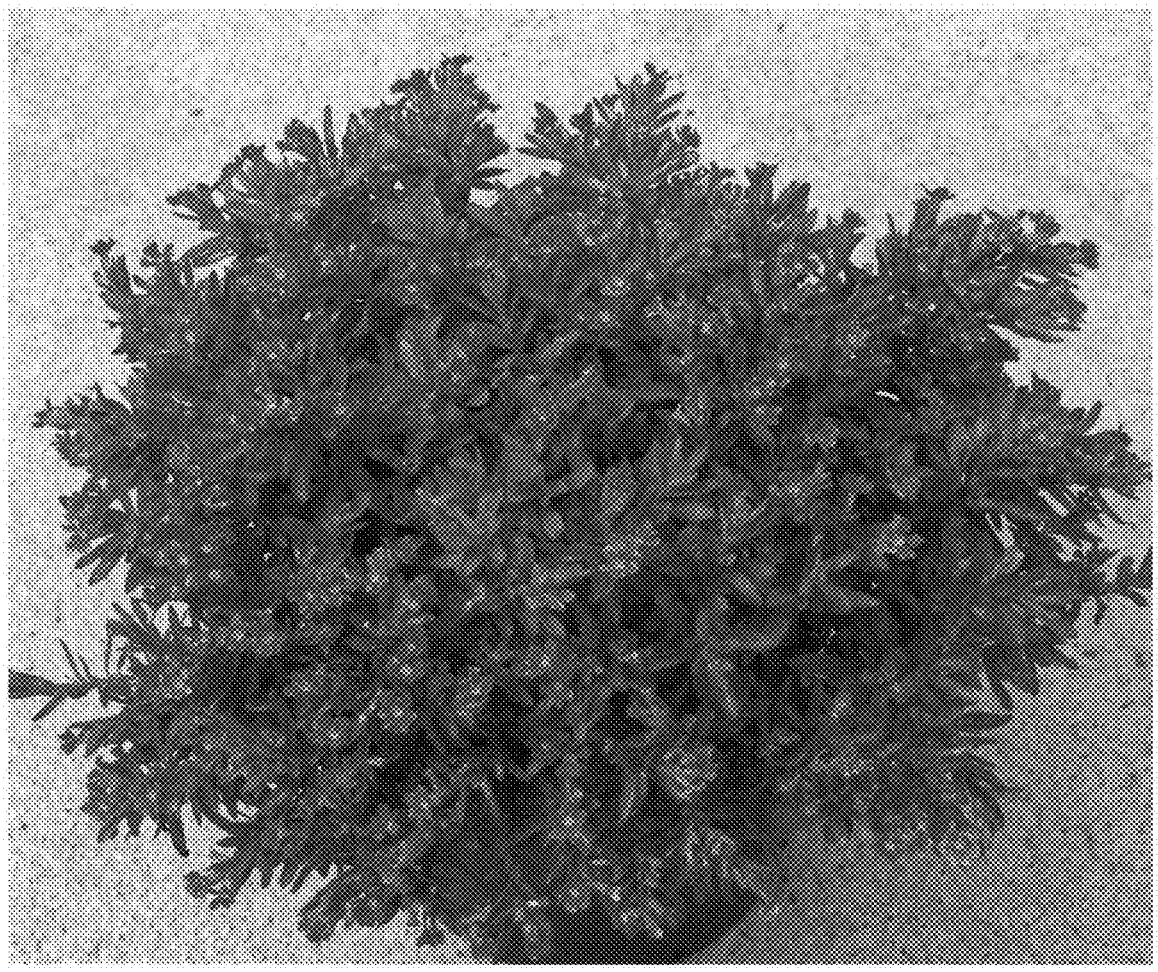

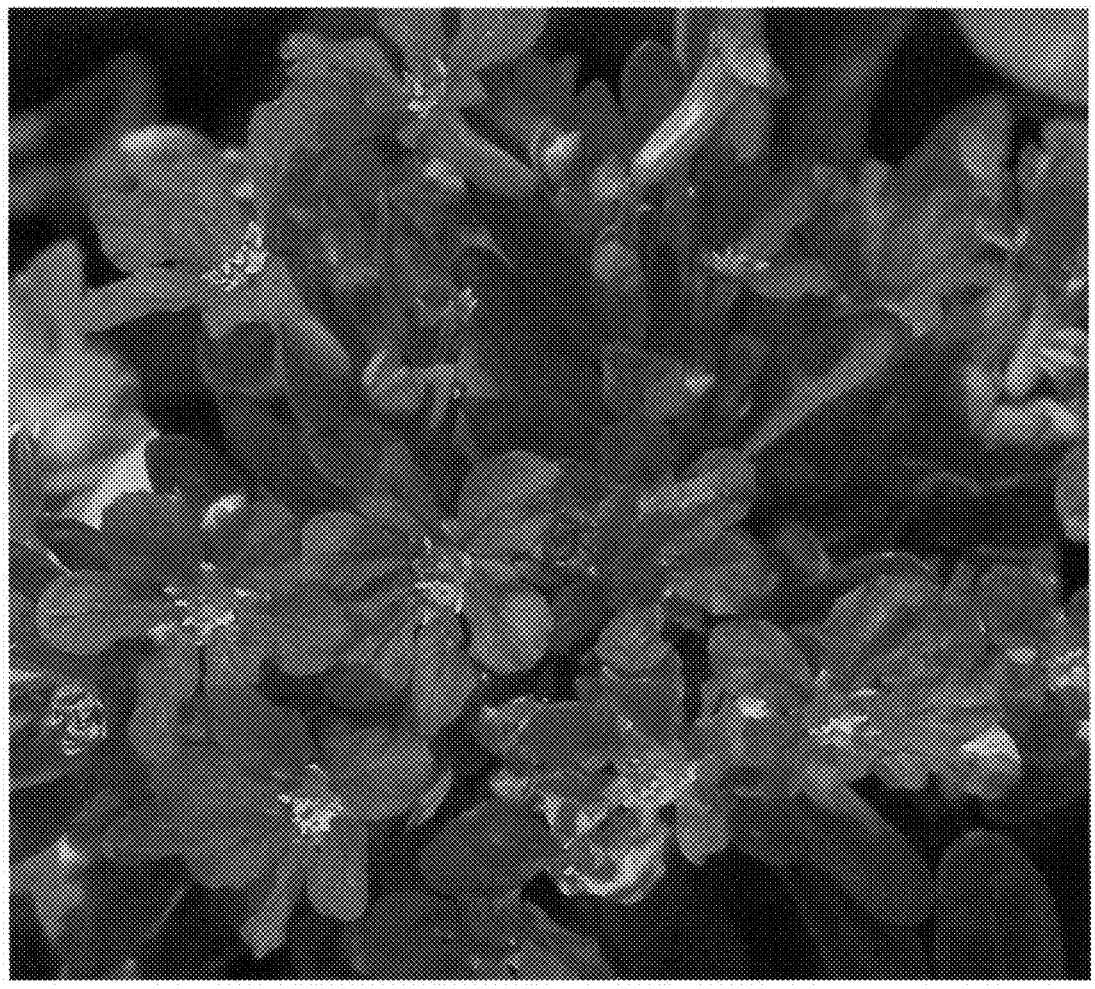

* * * * *